(12) United States Patent
Chen et al.

(10) Patent No.: US 8,809,343 B2
(45) Date of Patent: Aug. 19, 2014

(54) PYRIMIDINE DERIVATIVE, PREPARATION METHOD AND USE THEREOF

(75) Inventors: Fener Chen, Shanghai (CN); Yonghong Liang, Shanghai (CN); Zhaosen Zeng, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 13/142,076

(22) PCT Filed: Dec. 24, 2009

(86) PCT No.: PCT/CN2009/075931
§ 371 (c)(1),
(2), (4) Date: Sep. 12, 2011

(87) PCT Pub. No.: WO2010/072155
PCT Pub. Date: Jul. 1, 2010

(65) Prior Publication Data
US 2012/0122902 A1    May 17, 2012

(30) Foreign Application Priority Data

Dec. 26, 2008 (CN) .............................. 200810208011
Dec. 26, 2008 (CN) .............................. 200810208012
Jun. 18, 2009 (CN) .............................. 200910053345

(51) Int. Cl.
*A01N 43/54* (2006.01)
*A61K 31/517* (2006.01)
*C07D 239/02* (2006.01)

(52) U.S. Cl.
USPC ....................................... 514/258.1; 544/316

(58) Field of Classification Search
USPC ........................................ 544/316; 514/258.1
See application file for complete search history.

(56) References Cited

U.S. PATENT DOCUMENTS

| 7,491,732 | B2 * | 2/2009 | Li et al. ........................ | 514/275 |
| 2006/0148800 | A1 * | 7/2006 | Stadtmueller et al. ........ | 514/242 |
| 2006/0270694 | A1 * | 11/2006 | Wong ............................ | 514/275 |
| 2007/0197782 | A1 * | 8/2007 | Clough et al. ................ | 544/51 |
| 2008/0194605 | A1 * | 8/2008 | Heinrich et al. ............. | 514/275 |
| 2008/0306099 | A1 * | 12/2008 | Li et al. ........................ | 514/275 |
| 2011/0046108 | A1 * | 2/2011 | Kettle et al. .............. | 514/210.18 |

FOREIGN PATENT DOCUMENTS

| CN | 1486310 | 3/2004 |
| CN | 1697830 | 11/2005 |
| CN | 101031551 | 9/2007 |
| CN | 101121698 | 2/2008 |
| CN | 101282945 | 10/2008 |
| CN | 101463014 | 6/2009 |
| CN | 101602733 | 12/2009 |
| WO | 03/030909 | 4/2003 |
| WO | 2006/002422 | 1/2006 |
| WO | 2008/079907 | 7/2008 |

OTHER PUBLICATIONS

International Search Report of PCT/CN2009/075931 dated Apr. 1, 2010.
Liu et al., "Discovery of a new class of 4-anilinopyrimidines as potent c-Jun N-terminal kinase inhibitors: synthesis and SAR studies," Bioorganic & Medicinal Chemistry Letters 17, 2007, pp. 668-672.
Liang et al.," Design, synthesis, and SAR of naphthyl-substituted diarylpyrimidines as non-nucleoside inhibitors of HIV-1 reverse transcriptase," ChemMedChem, 2009, vol. 4, pp. 1537-1545.
Feng et al., "Structural modifications of DAPY analogues with potent anit-HIV-1 activity," ChemMedChem, 2009, vol. 4, pp. 219-224.
Nayana et al., "Insight into the structural requirements of proton pump inhibitors based on CoMFA and CoMSIA studies," Journal of Molecular Graphics and Modelling, 2008, vol. 27, pp. 233-243.
CA (American Chemical Society), CAN 143:326363, 1978, vol. 143, CAS RN=64778-44-5, 64778-48-9, 64778-69-4, 64778-70-7, 5 pages total.

* cited by examiner

*Primary Examiner* — Paul V. Ward
(74) *Attorney, Agent, or Firm* — Hamre, Schumann, Mueller & Larson, P.C.

(57) ABSTRACT

A pyrimidine derivative and the preparation method and use thereof. The said pyrimidine derivative is a diaryl pyrimidine derivative or a diaryl benzo pyrimidine derivative which has the structure shown as the Formula I and IV.

Present pyrimidine derivative can be used for the prevention or the treatment of HIV.

17 Claims, No Drawings

PYRIMIDINE DERIVATIVE, PREPARATION METHOD AND USE THEREOF

FIELD OF THE INVENTION

The present invention belongs to the technical field of medicament, and specifically relates to a pyrimidine derivative, its phamaceutically accepted salts, its hydrates and solvates, its polycrystalline and eutectics, its precursors and derivatives of the same biological function, and the preparation method and use thereof.

BACKGROUND ARTS

AIDS, i.e. acquired immune deficiency syndrome, is an epidemic caused by human immunodeficiency virus (HIV). During the process of HIV's reverse transcription from mRNA to DNA, reverse transcriptase (RT) performs a decisive function, and therefore becomes an important target for the design of anti-AIDS medicines.

Among the current studies of anti-HIV medicines, non-nucleoside reverse transcriptase inhibitors (NNRTIs) have become one of the hotspots in the field of pharmaceutical chemistry for the benefits of high efficiency and low toxicity and etc thereof. At present, 4 kinds of reverse transcriptase inhibitors have received FDA approval: Nevirapine, Delavirdine, Efavirenz and etravirine (TMC125). In addition, α-APA089439, HBY097 and TMC-278 are undergoing clinical studies. Classical NNRTIs are only effective against HIV-1, but ineffective against HIV-2.

Therefore, this field urgently needs a novel medicine to prevent or treat AIDS.

SUMMARY OF THE INVENTION

The present invention aims at providing a pyrimidine derivative, and the preparation method and use thereof.

One aspect of the present invention provides a diaryl pyrimidine derivative or pharmaceutically acceptable salts thereof; the diaryl pyrimidine derivative has the structure shown as the formula I:

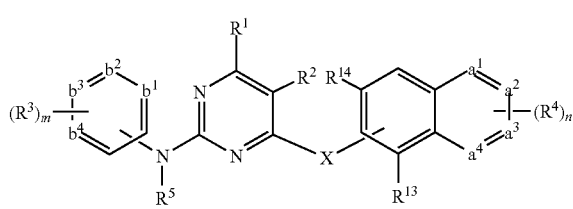

I wherein: -$a^1$=$a^2$-$a^3$=$a^4$- represents the structure of a divalent free radical: —CH=CH—CH=CH—, —N=CH—CH=CH—, —CH=N—CH=CH—, —N=N—CH=CH—, —N=CH—N=CH—, —N=CH—CH=N—;

-$b^1$=$b^2$-$b^3$=$b^4$- represents the structure of a divalent free radical: —CH=CH—CH=CH—, —N=CH—CH=CH—, —N=N—CH=CH—, —N=CH—N=CH—, —N=CH—CH=N—;

$R^1$ and $R^2$ respectively are separately selected from hydrogen, hydroxyl, halogen, substituted $C_{1-4}$ alkyl, substituted $C_{2-6}$ alkenyl, substituted $C_{2-6}$ alkynyl, $C_{1-6}$ alkoxyl, cyano-group, nitryl, amino-group, —NH(OH)—, —N($R^6$)p—;

$R^{13}$ and $R^{14}$ respectively are separately selected from hydrogen, hydroxyl, halogen, substituted $C_{1-4}$ alkyl, substituted $C_{2-6}$ alkenyl, substituted $C_{2-6}$ alkynyl, $C_{1-6}$ alkoxyl, cyano-group, nitryl, amino-group, —NH(OH)—, —N($R^6$)p—;

$R^3$ and $R^4$ respectively are separately selected from hydrogen, hydroxyl, halogen, optionally $C_{1-4}$ alkyl substituted by cyano-group or —C(=O)$R^6$, $C_{3-7}$ cycloalkyl, optionally $C_{2-6}$ alkenyl substituted by one or more halogen atoms or cyano-groups, optionally $C_{2-6}$ alkynyl substituted by one or more halogen atoms or cyano-groups, $C_{1-6}$ alkoxyl, $C_{1-6}$ alkoxycarbonyl, carboxyl, cyano-group, nitryl, amino-group, —NR$^5$—, methyl polyhalide, methoxyl polyhalide, methylthio polyhalide, —S(=O)$_p$R$^7$, —NH—S(=O)$_p$R$^7$, —C(=O)R$^7$, —NHC(=O)H, —C(=O)NHNH$_2$, —NHC(=O)R$^7$, —C(=NH)R$^7$;

$R^5$ represents hydrogen, $C_{1-6}$ alkycarbonyl, aryl, formoxyl, $C_{1-6}$ alkyl, $C_{1-6}$ alkoxycarbonyl;

X and Y are separately selected from —NR$^6$—, —NH—NH—, —N=N—, —O—, —C(=O)—, $C_{1-4}$ alkanediyl, —CHOH—, —S—, —S(=O)p—, -X$_1$-C$_{1-4}$ alkanediyl- or —C$_{1-4}$ alkanediyl-X$_1$-, —CH(CN)—;

X$_1$ represents —NR$^6$—, —NH—NH—, —N=N—, —O—, —C(=O)—, —CHOH—, —S(=O)p—;

$R^6$ is separately selected from hydrogen, aryl, formoxyl, $C_{1-6}$ alkycarbonyl, $C_{1-6}$ alkyl, $C_{1-6}$ alkoxycarbonyl, $C_{1-6}$ alkyl substituted by formoxyl, $C_{1-6}$ alkycarbonyl, $C_{1-6}$ alkoxycarbonyl or $C_{1-6}$ alkycarboxyl, $C_{1-6}$ alkoxyl or $C_{1-6}$ alkoxycarbonyl substituted by $C_{1-6}$ alkoxycarbonyl.

$R^7$ is selected from $C_{1-4}$ alkyl, amino-group-, —NH—NH—, mono- or di-($C_{1-4}$ alkyl) amino-group of $C_{1-4}$ alkyl polyhalide.

m is an integer from 0 to 5, n is an integer from 0 to 6;
P is an integer of 1 or 2.

In another preferred embodiment, the diaryl pyrimidine derivative has the structure shown as the formula II:

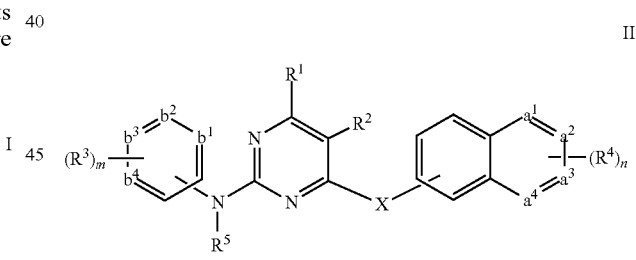

II

In another preferred embodiment, the diaryl pyrimidine derivative has the structure shown as the formula III:

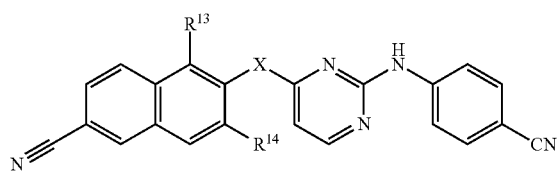

III

The diaryl pyrimidine derivative or the pharmaceutically acceptable salts thereof according to the present invention, the salts are selected from hydrochloride, sulfate, tartrate, citrate, fumarate, or malate.

The second aspect of the present invention provides a diaryl benzo pyrimidine derivative, N-oxides thereof, stereoisomerides, mixture of stereoisomerides, or pharmaceutically acceptable salts, the diaryl benzo pyrimidine derivative has the structure shown as the formula IV.

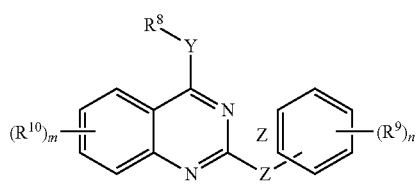

IV wherein $R^8$ is independently selected from aryl, naphthyl, substituted naphthyl, 5- or 6-membered aromatic heterocyclic, $C_{1-6}$ alkoxycarbonyl, aryloxycarbonyl, or substituted aryloxycarbonyl.

$R^9$ and $R^{10}$ respectively are separately selected from hydrogen, hydroxyl, halogen, $C_{1-6}$ alkoxyl, $C_{1-6}$ alkoxycarbonyl, carboxyl, cyano-group, nitryl, amino-group, —$NR^{11}$—, methyl polyhalide, methoxyl polyhalide, methylthio polyhalide, —$S(=O)_pR^{12}$, —NH—$S(=O)_pR^{12}$, —$C(=O)R^{12}$, —NHC(=O)H, —C(=O)NHNH$_2$, —NHC(=O)R$^{12}$, —C(=NH)R$^{12}$.

Z and Y respectively are separately selected from —$NR^{11}$—, —NH—, —NH—NH—, —N=N—, —O—, —C(=O)—, $C_{1-4}$ alkanediyl, —CH(OH)—, —S—, —S(=O)p—, -$X_2$-$C_{1-4}$ alkanediyl or -$C_{1-4}$ alkanediyl-$X_2$-, —CH(CN)—;

$X_2$ is selected from —$NR^{11}$—, —NH—NH—, —N=N—, —O—, —C(=O)—, —CH(OH)—, —S(=O)p—;

$R^{11}$ is separately selected from hydrogen, aryl, formoxyl, $C_{1-6}$ alkycarbonyl, $C_{1-6}$ alkyl, $C_{1-6}$ alkoxycarbonyl, $C_{1-6}$ alkyl substituted by formoxyl, $C_{1-6}$ alkycarbonyl, $C_{1-6}$ alkoxycarbonyl or $C_{1-6}$ alkycarboxyl, $C_{1-6}$ alkoxyl or $C_{1-6}$ alkoxycarbonyl substituted by $C_{1-6}$ alkoxycarbonyl;

$R^{12}$ is selected from $C_{1-4}$ alkyl, amino-group, mono- or di-($C_{1-4}$ alkyl) amino-group or $C_{1-4}$ alkyl polyhalide.

m is an integer from 0 to 5, n is an integer from 0 to 6;

P is an integer of 1 or 2.

The pharmaceutically acceptable salts of the diaryl benzo pyrimidine derivative according to the present invention, the pharmaceutically acceptable salts are selected from hydrochloride, sulfate, tartrate, citrate, fumarate, or malate.

The third aspect of the present invention provides a method for preparing a diaryl pyrimidine derivative, comprising the following steps:

(a) 4-chloro benzo pyrimidine derivative, substituted phenol or aniline, and polar aprotic solvent are mixed together to react according to the following general equation to obtain the diaryl benzo pyrimidine derivative;

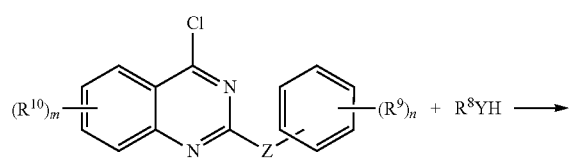

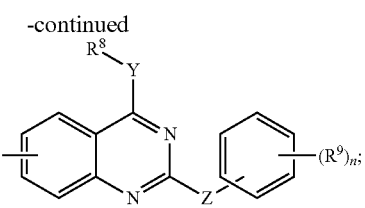

or, the process comprises the steps of:

(i) 2-chloro benzo pyrimidine derivative and substituted phenol or aniline are heated to 150° C.-210° C. to fuse to react according to the following general equation, to obtain the diaryl benzo pyrimidine derivative;

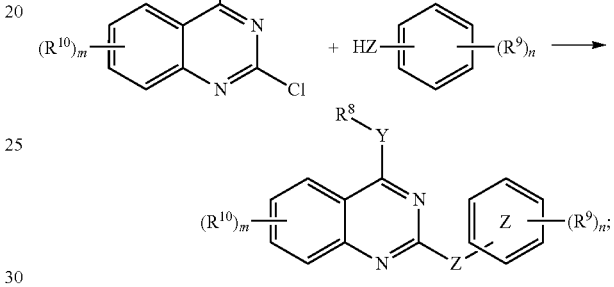

wherein, $R^8$ is separately selected from aryl, substituted aryl, naphthyl, substituted naphthyl, 5- or 6-membered aromatic heterocyclic, $C_{1-6}$ alkoxycarbonyl, aryloxycarbonyl, or substituted aryloxycarbonyl.

$R^9$ and $R^{10}$ respectively are separately selected from hydrogen, hydroxyl, halogen, $C_{1-6}$ alkoxyl, $C_{1-6}$ alkoxycarbonyl, carboxyl, cyano-group, nitryl, amino-group, —$NR^{11}$—, methyl polyhalide, methoxyl polyhalide, methylthio polyhalide, —$S(=O)_pR^{12}$, —NH—$S(=O)_pR^{12}$, —$C(=O)R^{12}$, —NHC(=O)H, —C(=O)NHNH$_2$, —NHC(=O)R$^{12}$, —C(=NH)R$^{12}$.

Z and Y respectively are separately selected from —$NR^{11}$—, —NH—, —NH—NH—, —N=N—, —O—, —C(=O)—, $C_{1-4}$ alkanediyl, —CH(OH)—, —S—, —S(=O)p—, -$X_2$-$C_{1-4}$ alkanediyl or -$C_{1-4}$ alkanediyl-$X_2$-, —CH(CN)—;

$X_2$ is selected from —$NR^{11}$—, —NH—NH—, —N=N—, —O—, —C(=O)—, —CH(OH)—, —S(=O)p—;

$R^{11}$ is separately selected from hydryogen, aryl, formoxyl, $C_{1-6}$ alkycarbonyl, $C_{1-6}$ alkyl, $C_{1-6}$ alkoxycarbonyl, $C_{1-6}$ alkyl substituted by formoxyl, $C_{1-6}$ alkycarbonyl, $C_{1-6}$ alkoxycarbonyl or $C_{1-6}$ alkycarboxyl, $C_{1-6}$ alkoxyl or $C_{1-6}$ alkoxycarbonyl substituted by $C_{1-6}$ alkoxycarbonyl;

$R^{12}$ is selected from $C_{1-4}$ alkyl, amino-group, mono- or di-($C_{1-4}$ alkyl) amino-group or $C_{1-4}$ alkyl polyhalide.

m is an integer from 0 to 5, n is an integer from 0 to 6;

P is an integer of 1 or 2.

In another preferred embodiment, the reaction of step (a) is carried out under the protection of inert gas; the inert gas is argon, nitrogen, helium, or combinations thereof.

In another preferred embodiment, the aprotic solvent used in step (a) is acetonitrile, N,N-dimethylformamide, N,N-dimethylacetamide, tetrahydrofuran, or combinations thereof.

In another preferred embodiment, bases is added during the reaction of step (a); the base is potassium carbonate, sodium carbonate, cesium carbonate, sodium hydride, sodium hydroxide, or potassium hydroxide.

The fourth aspect of the present invention provides a pharmaceutical composition; the pharmaceutical composition comprises effective dosage of diaryl pyrimidine derivative provided in the present invention or the pharmaceutically acceptable salts thereof; and pharmaceutically acceptable carriers.

The fifth aspect of the present invention provides a pharmaceutical composition; the pharmaceutical composition comprises effective dosage of diaryl benzo pyrimidine derivative provided in the present invention, N-oxides, stereoisomerides, mixture of stereoisomerides, or pharmaceutically acceptable salts thereof; and pharmaceutically acceptable carriers.

The sixth aspect of the present invention provides a use of the diaryl pyrimidine derivative provided in the present invention or the pharmaceutically acceptable salts thereof, for the manufacturing of a medicament for prevention or treatment of AIDS.

The seventh aspect of the present invention provides a use of the diaryl benzo pyrimidine derivative provided in the present invention, N-oxides, stereoisomerides, mixture of stereoisomerides, or pharmaceutically acceptable salts thereof, for the manufacturing of a medicament for prevention or treatment of AIDS.

Hereby, the present invention provides novel drugs to prevent or treat AIDS.

DETAILED DESCRIPTION OF THE INVENTION

Through intensive study, the inventor performed reorganization to the diaryl pyrimidine derivatives (DAPY), and simulated the action model and structure-activity relationship of such kind of inhibitor with HIV-1 RT, by means of computer aided drug design, here by to guide further structure improvement. Naphthyl group is introduced to C4-position of pyrimidine ring, to strengthen the π-π accumulation between the inhibitor and the surrounding residues of amino acids, Tyr188, Tyr181, Trp229, and Tyr318. Meanwhile, substitutional groups are introduced to C5-, C6-positions of pyrimidine ring, to strengthen its synergistic effect with naphthyl ring, and to disturb the catalytic function of the surrounding residues of amino acids. A series of diaryl pyrimidine derivatives are prepared and the biological activities thereof are tested. The results showed that most of the compounds have strong activities of anti HIV-1, and high selectivity index, and a part of the compounds show good inhibition activity against drug-resistant viral strain of L103N+Y181C.

The present invention provides a diaryl pyrimidine derivative or pharmaceutically acceptable salts thereof; the diaryl pyrimidine derivative has the structure shown as the formula I:

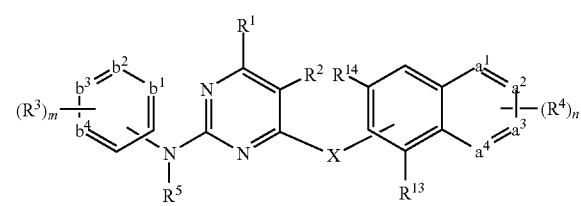

I

Preferably, the diaryl pyrimidine derivative provided in the present invention has the structure shown as the formula II:

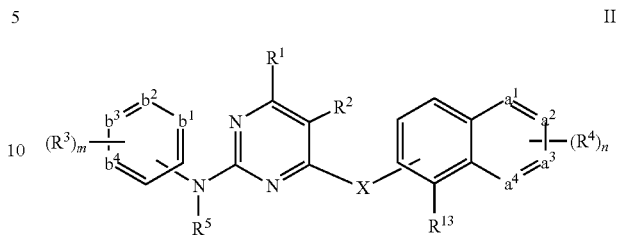

II wherein, -$a^1$=$a^2$-$a^3$=$a^4$- represents the structure of a divalent free radical: —CH=CH—CH=CH—, —N=CH—CH=CH—, —CH=N—CH=CH—, —N=N—CH=CH—, —N=CH—N=CH—, —N=CH—CH=N—;

-$b^1$=$b^2$-$b^3$=$b^4$- represents the structure of a divalent free radical: —CH=CH—CH=CH—, —N=CH—CH=CH—, —N=N—CH=CH—, —N=CH—N=CH—, —N=CH—CH=N—;

$R^1$ and $R^2$ respectively are separately selected from hydrogen, hydroxyl, halogen, substituted $C_{1-4}$ alkyl, substituted $C_{2-6}$ alkenyl, substituted $C_{2-6}$ alkynyl, $C_{1-6}$ alkoxyl, cyano-group, nitryl, amino-group, —NH(OH)—, —N($R^6$)p—;

$R^{13}$ and $R^{14}$ respectively are separately selected from hydrogen, hydroxyl, halogen, substituted $C_{1-4}$ alkyl, substituted $C_{2-6}$ alkenyl, substituted $C_{2-6}$ alkynyl, $C_{1-6}$ alkoxyl, cyano-group, nitryl, amino-group, —NH(OH)—, —N($R^6$)p—;

$R^{13}$ and $R^{14}$ respectively are separately selected from hydrogen, hydroxyl, halogen, substituted $C_{1-4}$ alkyl, substituted $C_{2-6}$ alkenyl, substituted $C_{2-6}$ alkynyl, $C_{1-6}$ alkoxyl, cyano-group, nitryl, amino-group, —NH(OH)—, —N($R^6$)p—;

$R^3$ and $R^4$ respectively are separately selected from hydrogen, hydroxyl, halogen, optionally $C_{1-4}$ alkyl substituted by cyano-group or —C(=O)$R^6$, $C_{3-7}$ cycloalkyl, optionally $C_{2-6}$ alkenyl substituted by one or more halogen atoms or cyano-groups, optionally $C_{2-6}$ alkynyl substituted by one or more halogen atoms or cyano-groups, $C_{1-6}$ alkoxyl, $C_{1-6}$ alkoxycarbonyl, carboxyl, cyano-group, nitryl, amino-group, —N$R^5$—, methyl polyhalide, methoxyl polyhalide, methylthio polyhalide, —S(=O)$_p$$R^7$, —NH—S(=O)$_p$$R^7$, —C(=O)$R^7$, —NHC(=O)H, —C(=O)NHNH$_2$, —NHC(=O)$R^7$, —C(=NH)$R^7$;

$R^5$ represents hydrogen, $C_{1-6}$ alkycarbonyl, aryl, formoxyl, $C_{1-6}$ alkyl, $C_{1-6}$ alkoxycarbonyl;

X and Y are separately selected from —N$R^6$—, —NH—NH—, —N=N—, —O—, —C(=O)—, $C_{1-4}$ alkanediyl, —CHOH—, —S—, —S(=O)p—, -$X_1$-$C_{1-4}$ alkanediyl- or -$C_{1-4}$ alkanediyl-$X_1$-, —CH(CN)—;

$X_1$ represents —N$R^6$—, —NH—NH—, —N=N—, —O—, —C(=O)—, —CHOH—, —S(=O)p—;

$R^6$ is separately selected from hydrogen, aryl, formoxyl, $C_{1-6}$ alkycarbonyl, $C_{1-6}$ alkyl, $C_{1-6}$ alkoxycarbonyl, $C_{1-6}$ alkyl substituted by formoxyl, $C_{1-6}$ alkycarbonyl, $C_{1-6}$ alkoxycarbonyl or $C_{1-6}$ alkycarboxyl, $C_{1-6}$ alkoxyl or $C_{1-6}$ alkoxycarbonyl substituted by $C_{1-6}$ alkoxycarbonyl.

$R^7$ is selected from $C_{1-4}$ alkyl, amino-group-, —NH—NH—, mono- or di-($C_{1-4}$ alkyl) amino-group of $C_{1-4}$ alkyl polyhalide.

m is an integer from 0 to 5, n is an integer from 0 to 6;
P is an integer of 1 or 2.

The method for preparing the compound shown as the formula II is as following:

(1) A diaryl pyrimidine derivative wherein $R^1$ is H, Cl, $C_{1-4}$ alkyl, $C_{2-6}$ alkynyl, $C_{2-6}$ alkenyl is prepared according to the reference (CN200710045937.0), and the general equation is as following:

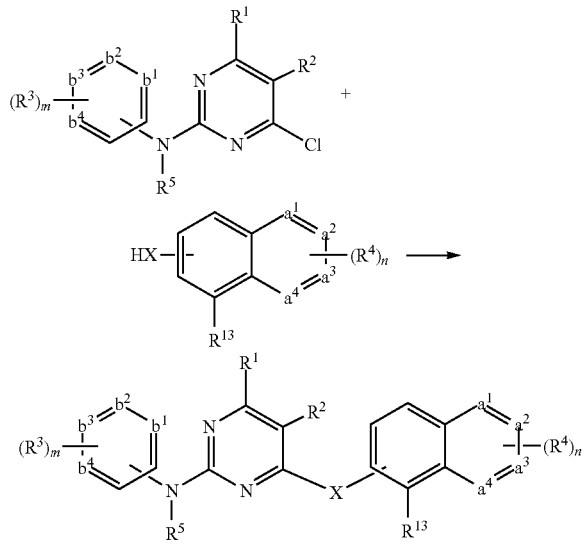

(2) The diaryl pyrimidine derivative wherein $R^1$ is $C_{1-6}$ alkoxyl is prepared with the diaryl pyrimidine derivative substituted by Cl as the reactant to react with $C_{1-6}$ sodium alkoxide, the reaction equation is as following:

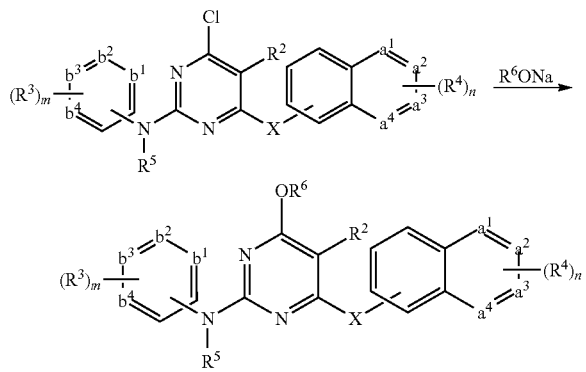

(3) The diaryl pyrimidine derivative wherein $R^1$ is aminogroup or —N($R^6$)p— (p=1,2) is prepared with the diaryl pyrimidine derivative substituted by Cl as reactant to react with alkanamine individually, the reaction equation is as following:

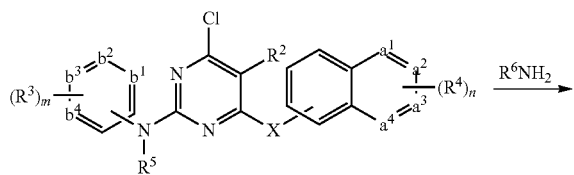

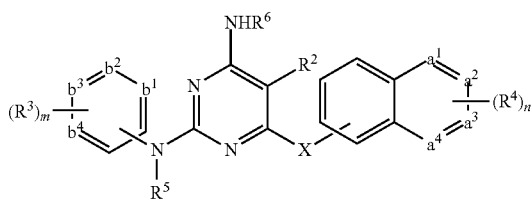

The compound shown as the formula II is an easily synthesized and completely novel anti-HIV reagent, and may be used as a candidate anti-HIV drug. The biological activity in the level of cells showed that: (1) this type of compounds generally possess good anti-HIV activity, and a part of the compounds not only show biological activity on nmol level, but also show high selectivity index. (2) Among the synthesized compounds, a part of the compounds show good inhibition activity against drug-resistant viral strain of L103N+ Y181C.

More preferably, the diaryl pyrimidine derivative synthesized in the present invention has the structure shown as the formula III:

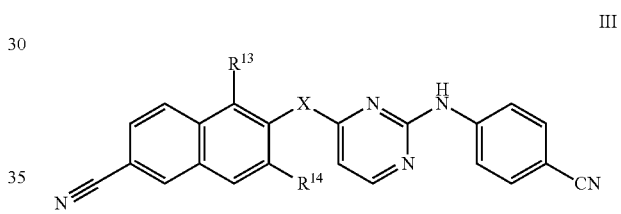

wherein, $R^{13}$ and $R^{14}$ respectively are separately selected from hydrogen, hydroxyl, halogen, substituted $C_{1-4}$ alkyl, substituted $C_{2-6}$ alkenyl, substituted $C_{2-6}$ alkynyl, $C_{1-6}$ alkoxyl, cyano-group, nitryl, amino-group, —NH(OH)—, —N($R^6$)p—;

X is selected from —$NR^6$—, —NH—NH—, —N=N—, —O—, —C(=O)—, $C_{1-4}$ alkanediyl, —CHOH—, —S—, —S(=O)p—, -$X_1$-$C_{1-4}$ alkanediyl- or -$C_{1-4}$ alkanediyl-$X_1$-, —CH(CN)—;

$X_1$ is selected from —$NR^6$—, —NH—NH—, —N=N—, —O—, —C(=O)—, —CHOH—, —S(=O)p—;

$R^6$ is separately selected from hydrogen, aryl, formoxyl, $C_{1-6}$ alkycarbonyl, $C_{1-6}$ alkyl, $C_{1-6}$ alkoxycarbonyl, $C_{1-6}$ alkyl substituted by formoxyl, $C_{1-6}$ alkycarbonyl, $C_{1-6}$ alkoxycarbonyl or alkycarboxyl, $C_{1-6}$ alkoxyl or $C_{1-6}$ alkoxycarboxyl substituted by $C_{1-6}$ alkoxycarboxyl.

P is an integer of 1 or 2.

The method for preparing the compound shown as the formula III is as following:

(1) $R^{13}$ and $R^{14}$ are H, Cl, $C_{1-4}$ alkyl, $C_{2-6}$ alkynyl, $C_{2-6}$ alkenyl respectively. The diaryl pyrimidine derivative, wherein X is O, is prepared according to the reference (CN200710045937.0); the general reaction equation is as following:

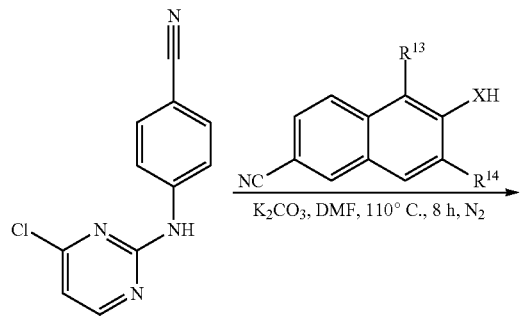

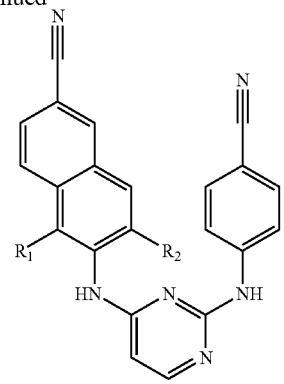

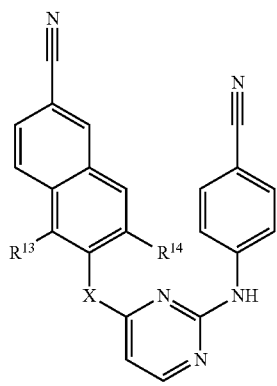

i.e., under the protection of inert gas, substituted naphthol is added to anhydrous aprotic solvent and agitated to dissolve, then 4-chloro pyrimidine derivative is added and agitated to dissolve, after the addition of anhydrous $K_2CO_3$, the temperature is controlled at 90~100° C., the system is agitated to keep reaction for 8~12 h. When TLC shows that the reaction is complete, $K_2CO_3$ is filtered out, and the filtrate is poured into cold water, the crystal is filtered out and dried. The desired compound is achieved by recrystallization with toluene or dioxane and etc., or by column chromatography.

(2) $R^{13}$ and $R^{14}$ are H, Cl, $C_{1-4}$ alkyl, $C_{2-6}$ alkynyl, $C_{2-6}$ alkenyl respectively; the general reaction equation of preparing the diaryl pyrimidine derivative wherein X is nitrogen is as following:

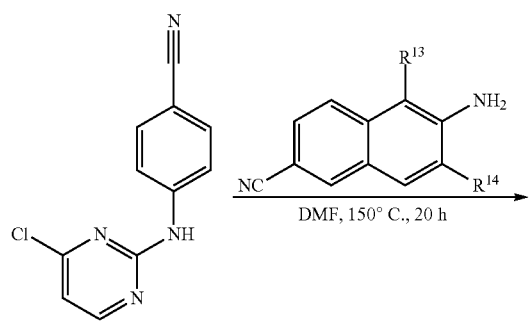

Substituted naphthylamine is dissolved in DMF, then 4-chloro pyrimidine is added and agitated to dissolve, and heated under reflux for 20 h in an oil bath at 150° C., the reaction mixture is poured into cold water and the deposited solid is filtered out and dried. The desired compound is obtained by recrystallization with toluene or dioxane and etc., or by column chromatography.

The compound shown as the formula III is an easily synthesized and completely novel anti-HIV reagent, and may be used as a candidate anti-HIV drug. The biological activity in the level of cells showed that: (1) this type of compounds generally possess good anti-HIV activity, and a part of the compounds not only show biological activity on nmol level, but also show high selectivity index. (2) Among the synthesized compounds, a part of the compounds show good inhibition activity against drug-resistant viral strain of L103N+ Y181C.

Therefore, the present invention provides a pharmaceutical composition, the composition consists effective dosage of the diaryl pyrimidine derivative shown as the formula I, II, or III, or pharmaceutically acceptable salts thereof; and pharmaceutically acceptable carriers.

As used herein, the terms of "containing" or "comprising" comprise "including", "basically be consisted of", and "be consisted of".

As used herein, the components of the term of "pharmaceutically acceptable" or "bromatologically acceptable" are those suitable to human and/or animals without excess adverse-effect (such as toxicity, irritant and allergic reaction), i.e. the substances possessing reasonable ratio of benefits and risk.

As used herein, the term of "effective dosage" refers to the amount that is sufficient to achieve the desired function or activity on human and/or animal and can be accepted by human and/or animal.

As used herein, the term of "pharmaceutically acceptable carriers" refers to the carriers of medicaments, including all kinds of excipients and diluents. The term refers to such kinds of carriers: they are not necessary active components, and possessing no excess toxicity after application. Suitable carriers are well known to those skilled in the art. Full discussion on pharmaceutically acceptable carriers can be found in Remington's Pharmaceutical Sciences (Mack Pub. Co., N.J. 1991). The pharmaceutically acceptable carriers used in the pharmaceutical compositions can be liquid, such as water, brine, glycerol and alcohol. Additionally, auxiliary substances can be existed in the carriers, such as fillers, disintegrating agents, lubricants, flow aids, effervescent agents, wetting agents or emulsifiers, corrigents, pH buffer substances and etc.

The present invention provides a diaryl benzo pyrimidine derivative, N-oxides, stereoisomerides, mixture of stereoisomerides, or pharmaceutically acceptable salts thereof, the diaryl benzo pyrimidine derivative has the structure shown as the formula IV:

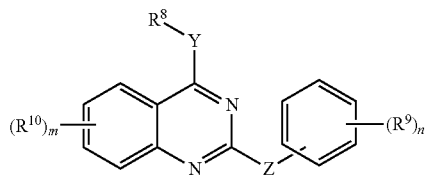

IV wherein $R^8$ is independently selected from aryl, substituted aryl, naphthyl, substituted naphthyl, 5- or 6-membered aromatic heterocyclic, $C_{1-6}$ alkoxycarbonyl, aryloxycarbonyl, or substituted aryloxycarbonyl;

$R^9$ and $R^{10}$ respectively are separately selected from hydrogen, hydroxyl, halogen, $C_{1-6}$ alkoxyl, $C_{1-6}$ alkoxycarbonyl, carboxyl, cyano-group, nitryl, amino-group, $-NR^{11}-$, methyl polyhalide, methoxyl polyhalide, methylthio polyhalide, $-S(=O)_pR^{12}$, $-NH-S(=O)_pR^{12}$, $-C(=O)R^{12}$, $-NHC(=O)H$, $-C(=O)NHNH_2$, $-NHC(=O)R^{12}$, $-C(=NH)R^{12}$;

Z and Y respectively are separately selected from $-NR^{11}-$, $-NH-$, $-NH-NH-$, $-N=N-$, $-O-$, $-C(=O)-$, $C_{1-4}$ alkanediyl, $-CH(OH)-$, $-S-$, $-S(=O)p-$, $-X_2-C_{1-4}$ alkanediyl or $-C_{1-4}$ alkanediyl-$X_2$-, $-CH(CN)-$;

$X_2$ is selected from $-NR^{11}-$, $-NH-NH-$, $-N=N-$, $-O-$, $-C(=O)-$, $-CH(OH)-$, $-S(=O)p-$;

$R^{11}$ is separately selected from hydrogen, aryl, formoxyl, $C_{1-6}$ alkycarbonyl, $C_{1-6}$ alkyl, $C_{1-6}$ alkoxycarbonyl, $C_{1-6}$ alkyl substituted by formoxyl, $C_{1-6}$ alkycarbonyl, $C_{1-6}$ alkoxycarbonyl or $C_{1-6}$ alkycarboxyl, $C_{1-6}$ alkoxyl or $C_{1-6}$ alkoxycarbonyl substituted by $C_{1-6}$ alkoxycarbonyl;

$R^{12}$ is selected from $C_{1-4}$ alkyl, amino-group, mono- or di-($C_{1-4}$ alkyl) amino-group or $C_{1-4}$ alkyl polyhalide;

m is an integer from 0 to 5, n is an integer from 0 to 6;

P is an integer of 1 or 2.

The method for preparing the compound shown as the formula III is as following:

Method One:

4-chloro benzo pyrimidine derivative is reacted with the corresponding substituted phenol (or phenylamine and etc.) under the exsistence of $K_2CO_3$ to obtain the product of the present invention, the general reaction equation is as following:

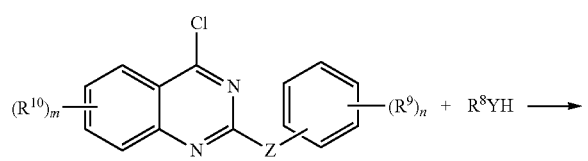

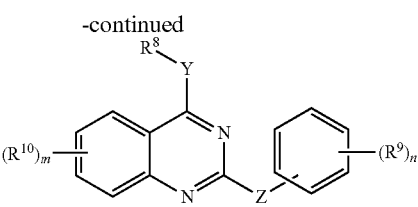

The detailed steps are as following: under the protection of inert gas, substituted phenol (or phenylamine and etc.) is added to anhydrous aprotic solvent and agitated to dissolve, then 4-chloro benzo pyrimidine derivative is added and agitated to dissolve, after the addition of anhydrous potassium carbonate, the system is agitated to keep reaction for 8~12 h at 80~120° C. When TLC shows that the reaction is complete, $K_2CO_3$ is filtered out, and the filtrate is poured into cold water, the crystal is filtered out and dried. The desired compound is obtained through decoloring by activated carbon and recrystallization with toluene.

More preferably, the molar ratio of 4-chloro benzo pyrimidine derivative and substituted phenol (or phenylamine and etc.) is 1:1.2~1:1.5. Anhydrous $K_2CO_3$ should be greatly excess, approximately be 5 times of the amount of substituted phenol; the aprotic solvent is DMF, DEA, acetonitrile; 1 mmol 4-chloro benzo pyrimidine derivative needs 6~8 mL aprotic solvent; the inert gas is nitrogen, argon and etc.

Method Two:

2-chloro benzo pyrimidine derivative is reacted with the corresponding substituted phenol (or phenylamine and etc.) in solvent-free conditions to obtain the product of the present invention; the general reaction equation is as following:

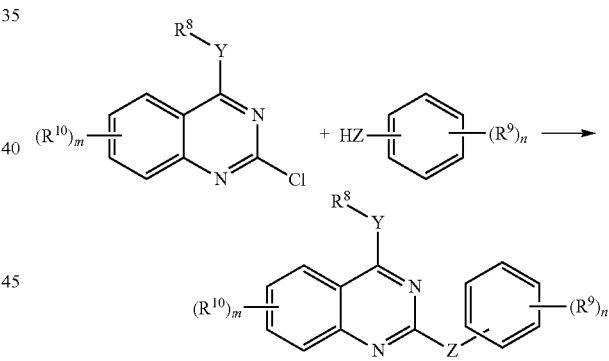

The detailed steps are as following: substituted phenol (or phenylamine and etc.) are mixed together, and heated to 150° C.-210° C. until the reactants are completely fused, and kept reaction for 1 h. When TLC shows that the reaction is complete, the reaction mixture is dissolved in DMF, decolored with activated carbon, and filtered, the filtrate is poured into cold water. The solid is filtered out and dried. The desired compound is obtained through recrystallization with toluene.

The compound shown as the formula IV is an easily synthesized and completely novel anti-HIV reagent, and may be used as a candidate anti-HIV drug. The biological activity in the level of cells showed that: this type of compounds generally possesses good anti-HIV activity, and a part of the compounds not only show biological activity on nmol level, but also show high selectivity index.

Therefore, the present invention provides a pharmaceutical composition, the composition comprises effective amount of the diaryl benzo pyrimidine derivative shown as the formula IV, N-oxides, stereoisomerides, mixture of stereoisomerides, or pharmaceutically acceptable salts therefore; and pharmaceutically acceptable carriers.

The characteristics mentioned in the present invention or in the embodiments can be free to combine.

The main benefits of the present invention are as follows:

1. The compound provided in the present invention possesses novel structure, and good anti HIV biological activity, and slight cell toxicity.

2. The preparation method of the compound provided in the present invention is easy, and can be further developed as anti-AIDS drugs.

The present invention will be further explained in respect of the various embodiments below. It is to be understood that the embodiments serve to explain only, without limitation the scope of the present invention. The experimental processes of the following embodiments where the conditions are not listed should be carried out generally according to the regular conditions or according to the suggested conditions by manufacturers. Unless specifically stated to the contrary, percents, ratios, proportions, or parts herein are all by weight.

The units of the weight volume percent herein are familiar to those skilled in the art, such as applied to refer to the weight of the solute in 100 mL solution.

Unless specifically defined to the contrary, all the specialized or scientific terms herein possess the same meaning as that known to those skilled in the art. Additionally, any process or material similar or equivalent to the records can be applied in the process of the present invention. The preferred embodiments and materials herein serve to demonstrate only.

Anti-HIV Biological Activity Test in the Embodiments of the Present Invention

Anti-virus activity of cells in vitro was determined by Rega Institute for Medical of Spain Katholleke University, consisting mainly: inhibitory activity towards HIV-infected MT-4 cells and cell toxicity. The method is described below: exert the compound on the HIV-infected ME-4 cells, and determine the protection of the drug on the cell lesions induced by HIV at varied HIV-infection intervals, calculate the half effective concentration $IC_{50}$, the required concentration that protect 50% of cells from cell lesions induced by HIV. Toxicity determination is carried out in parallel with anti-HIV activity experiments, also in the cultured MT-4 cells, determine the $CC_{50}$, the concentration that leads 50% of uninfected cells to cell lesions, and calculate the selectivity index $SI=CC_{50}/IC_{50}$ with the MTT method.

Materials and Methods

Anti-HIV activity of various compounds is monitored by the inhibitory efficiency of drugs on the cell lesions induced by HIV. Carry out cell culture with MT-4 cells. The adopted virus strains are HIV-1 IIIB strain and drug-resistant viral strain of L103N+Y181C.

The detailed operation is as follows: the compound is dissolved with DMSO or water and diluted with phosphate buffer saline, $3 \times 10^5$ MT-4 cells are cultured with 100 μL various concentrations of compounds for 1 h, then 100 μL suitable virus dilution is added to the compound, and the cells are cultured at 37° C. for 1 h. After being washed for 3 times, the cells are suspended again in the culture media containing or not compounds individually. Subsequently, the cells are transferred to the atmosphere containing 5% $CO_2$ and cultured for 7 days at 37° C., and culture media containing or not compounds are used to replace or supplement the culture solution on the third day after infection. Kinds of culture conditions should be duplicated. The cell lesions caused by virus are monitored with reverse light microscopy everyday. Typically, the virus dilution applied in the present experiments generally cause cell lesion on the fifth day after infection. Inhibitory concentration of a drug is expressed with the concentration that is required for 50% inhibition of cell lesions ($EC_{50}$) caused by virus and meanwhile shows no direct toxicity to cells ($CC_{50}$). It should be emphasized that, when the compound is poorly water-soluble and can only be dissolved in DMSO, the ratio of DMSO to water is generally below 10% (the final concentration of DMSO in MT-4 cell culture media is smaller than 2%). Because DMSO can influence the anti-virus activity of the tested compounds, blank tests on the solution containing the same concentration of DMSO should be conducted in parallel. Additionally, the final concentration of DMSO is far below the concentration required to influence the replication of HIV-1 in T cells.

Example 1

Synthesis of the Diaryl Pyrimidine

Under the protection of inert gas, naphthol was added to anhydrous aprotic solvent, and agitated to dwassolve, then 4-chloro pyrimidine derivative was added and agitated to dissolve, after addition of anhydrous $K_2CO_3$, the temperature was controlled at 90~100° C. and the system was agitated to keep reaction for 8~12 h. When TLC shows that the reaction was complete, $K_2CO_3$ was filtered out, and the filtrate was poured into cold water, the deposited crystal was filtered out and dried. The desired compound was obtained through decoloring by activated carbon and recrystallization with toluene.

Target compounds were prepared by the above mentioned process with various 4-chloro pyrimidine derivatives and various substituted naphthols, parts of the results are as follows:

Under the protection of $N_2$, 8-hydroxy quinoline (4.2 mmol) was added to 30 mL anhydrous DMF and agitated to dissolve, then 2-(4-cyanoanilino)-4-chloro methyl pyrimidine (3.5 mmol) was added and agitated for 10 min to dissolve, after addition of anhydrous $K_2CO_3$ (0.021 mol), the temperature was controlled at 80° C. and the system was agitated to keep reaction for 8 h. When TLC shows that the reaction was complete, $K_2CO_3$ was filtered out, and the filtrate was poured into 300 mL cold water, solid was deposited; the solid was filtered out and dried and the crude product was prepared. The desired compound 1 was achieved through decoloring by activated carbon and recrystallization with toluene.

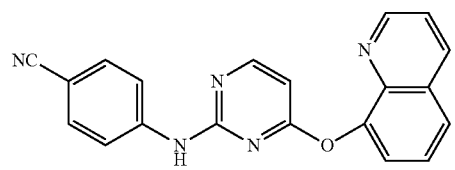

1

Brown powder, yield: 87%: mp: 178.6-181.5° C.; $^1$HNMR (DMSO, 400 MHz) $\delta_{ppm}$: 6.74(d, J=5.6Hz, 1H, CH), 7.21-7.28(m, 4H, Ph), 7.57-8.83(m, 6H, Quin), 8.45(d, J=5.6Hz, 1H, CH), 9.98(s, 1H, NH).

Under the protection of $N_2$, 8-hydroxy quinoline (5.2 mmol) was added to 30 mL anhydrous acetonitrile and agitated to dissolve, then 2-(4-Cyanoanilino)-4,6-dichloro pyrimidine (5.2 mmol) was added and agitated for 10 min to dwassolve, after addition of anhydrous $K_2CO_3$ (0.021 mol), the temperature was controlled at 90~100° C. and the system was agitated to keep reaction for 8 h. When TLC shows that the reaction was complete, K₂CO₃ was filtered out, and the filtrate was poured into 300 mL cold water, solid was deposited; the solid was filtered out and dried and the crude product was prepared. The desired compound 2 was achieved through decoloring by activated carbon and recrystallization with toluene.

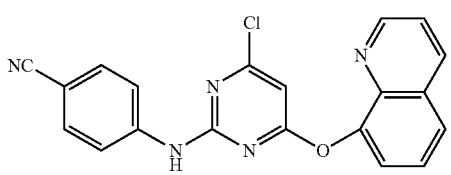

2

Green powder, yield: 85%; mp:138.4-141.4° C.; ¹HNMR (DMSO, 400 MHz) δ$_{ppm}$: 6.92(s, 1H, CH), 7.06-7.24(m, 4H, Ph), 7.55-8.82(m, 6H, Quin), 10.33(s, 1H, NH).

The prepared compound 2 (2 mmol) above was dissolve in 25 mL dioxane, and agitated to dissolve, then 5 mL methylamine alcohol solution was added, and the temperature was controlled at 140-150° C., and the system was agitated to keep reaction for 12 h. When TLC shows that the reaction was complete, compound 3 was achieved by recrystallization with water.

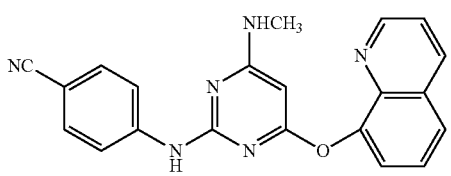

3

White powder, yield: 68%, mp: 231.4-232.1° C.; ¹HNMR (DMSO, 400 MHz) δ$_{ppm}$: 2.82(s, 3H, NHCH₃), 5.50(s, 1H, CH), 7.20 (s, 1H, NHCH₃), 7.34-7.79 (m, 4H, Ph), 7.48-8.72 (m, 6H, Quin), 9.46(s, 1H, NH).

Sodium (10 mmol) was dissolved in 50 mL anhydrous methol, and agitated to dissolve, then the prepared compound 2 was added, and the temperature was controlled at 40-50° C., the system was agitated to keep reaction for 48 h. When TLC shows that the reaction was complete, compound 4 was achieved by recrystallization with water.

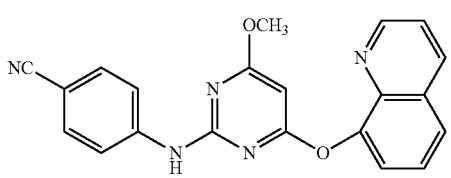

4

White powder, yield: 92%; mp: 231.4-232.1° C.; ¹HNMR (DMSO, 400 MHz) δ$_{ppm}$: 3.92(s, 3H, OCH₃), 6.02(s, 1H, CH), 7.17-7.32(m, 4H, Ph), 7.54-8.82(m, 6H, Quin), 9.87(s, 1H, NH).

Example 2

Synthesis of the Diaryl Pyrimidine Derivative

Under the protection of inert gas, substituted naphthol was added to anhydrous aprotic solvent, and agitated to dissolve, then 4-chloro pyrimidine derivative was added and agitated to dissolve, after addition of anhydrous K₂CO₃, the temperature was controlled at 90~100° C., the system was agitated to keep reaction for 8~12 h. When TLC shows that the reaction was complete, K₂CO₃ was filtered out, and the filtrate was poured into 300 mL cold water, solid was deposited; the solid was filtered out and dried. The desired compound was obtained through column chromatography or recrystallization.

Target compounds were prepared by the above mentioned process with 4-chloro pyrimidine derivatives and various substituted naphthols; parts of the results are as following:

Under the protection of N₂, β-naphthol derivative (4.2 mmol) was added to 30 mL anhydrous DMF, and agitated to dissolve, then 2-(4-Cyanoanilino)-4-methyl pyrimidine (3.5 mmol) is added and agitated for 10 min to dissolve, after addition of anhydrous K₂CO₃, the temperature is controlled at 90~100° C., the system was agitated to keep reaction for 8 h. When TLC shows that the reaction was complete, the filtrate was poured into 300 mL cold water, solid was deposited; the solid was filtered out and dried and the crude product was prepared. The desired compound 20 was achieved through column separation.

20

White powder, yield: 89.3%; mp 249.2-250.1° C.; ¹H NMR (400 MHz, DMSO-d₆) δ 3.90 (s, 3H, CH₃), 6.76 (d, 1H, J=4.0 Hz, CH), 7.25-7.55 (m, 4H, Ph), 7.64-8.50 (m, 5H, Naph), 8.71 (s, 1H, CH), 10.10 (s, 1H, NH); ¹³C NMR (400 MHz, DMSO-d₆) δ 61.77, 99.70, 102.55, 108.66, 118.22, 118.99, 119.27, 123.33, 125.13, 126.97, 129.96, 131.14, 132.42, 143.19, 144.35, 146.29, 158.98, 160.42, 168.97. MS (EI) m/z: 393.1 (M+); Anal. (C₂₃H₁₅N₆O₂) C, H, N.

21

White powder, yield: 41.8%; mp 249.3-250.4° C.; ¹H NMR (400 MHz, DMSO-d₆)δ 3.85 (s, 3H, OCH₃), 3.91 (s, 3H, OCH₃), 6.78 (d, J=4.0Hz, 1H), 7.24-7.52 (m, 4H, Ph), 7.54-8.54 (m, 4H, Naph), 8.49 (d, J=4.0Hz, 1H); ¹³C NMR (400 MHz, DMSO-d₆) δ 56.83, 62.23, 99.77, 102.98, 104.10, 109.61, 118.62, 119.63, 119.76, 123.76, 125.20, 125.46, 131.61, 132.93, 133.28, 135.82, 144.87, 148.00, 153.19, 160.83, 169.18. MS (EI) m/z: 423.2 (M+); Anal. (C₂₄H₁₇N₅O₃) C, H, N.

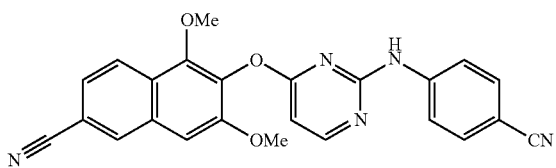

22

White powder, yield: 85.9%, mp 253.2-254.8 °C; $^1$H NMR (400 MHz, DMSO-d$_6$) δ 12 $^{13}$C NMR (400 MHz, DMSO-d$_6$) δ 3.83 (s, 3H, OCH$_3$), 6.69 (d, J=5.6Hz, $^1$H), 7.28-7.67 (m, 4H, Ph), 7.54-8.52 (m, 5H, Naph), 8.45 (d, J=5.6Hz, 1H), 10,07 (s, 1H, NH); $^{13}$C NMR (400 MHz, DMSO-d$_6$) δ 56.63, 99.94, 102.97, 108.98, 109.02, 118.66, 119.79, 119.81, 121.34, 125.39, 129.25, 130.47. 131.98, 132.98, 133.04, 144.47, 144.92, 152.33, 159.40. 160.67, 169.56. MS (EI) m/z: 393.1 (M+); Anal. (C$_{23}$H$_{15}$N$_6$O$_2$) C, H, N.

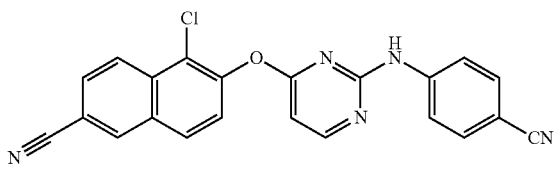

23

White powder, yield: 71.6%, mp 297.5-298.7 °C; $^1$H NMR (400 MHz, DMSO-d$_6$) δ 6.82 (d, J=4.0Hz, 1H), 7.27-7.52 (m, 4H, Ph), 8.02-8.54 (m, 5H, Naph), 8.82 (s, 1H, CH), 10.12 (s, 1H, NH); $^{13}$C NMR (400 MHz, DMSO-d$_6$) δ 100.18, 103.15, 109.78, 118.81, 119.09, 119.72, 123.09, 125.27, 125.55, 129.19, 130.08, 131.49, 132.81, 132.93, 135.93, 144.72, 159.33, 161.18, 168.88. MS (EI) m/z: 393.1 (M+); Anal. (C$_{22}$H$_{12}$ClN$_5$O) C, H, N, Cl.

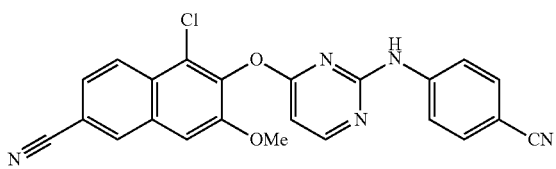

24

White powder, yield: 33.4%, mp: 268.4-269.2 °C; $^1$H NMR (400 MHz, DMSO-d$_6$) δ 12 $^{13}$C NMR (400 MHz, DMSO-d$_6$) δ 3.89 (s, 3H, CH$_3$), 6.82 (d, J=4.4Hz, 1H), 7.25-7.49 (m, 4H, Ph), 7.82-8.63 (m, 4H, Naph), 8.52 (d, J=4.4Hz, 1H), 10.11 (s, 1H, NH); $^{13}$C NMR (400 MHz, DMSO-d$_6$) δ 57.21, 99.71, 103.15, 108.27, 110.23, 118.66, 119.25, 119.72, 124.69, 125.54, 126.74, 127.57, 131.95, 132.94, 133.76, 141.45, 144.75, 152.66, 159.35, 161.13, 168.47. MS (EI) m/z: 427.1 (M+); Anal. (C$_{23}$H14ClN$_5$O2) C, H, N, Cl.

Example 3-1

Synthesis of the Diaryl Benzo Pyrimidine Derivative (Method One)

Under the protection of inert gas, substituted phenol (or phenylamine and etc.) is added to aprotic solvent, and agitated to dissolve, and then 4-choloro benzo pyrimidine derivative is added and agitated to dissolve, after addition of anhydrous K$_2$CO$_3$, the temperature is controlled at 80~120° C. and the system was agitated to keep reaction for 8~12 h. When TLC shows that the reaction was complete, K$_2$CO$_3$ was filtered out, and the filtrate was poured into cold water, the deposited crystal was filtered out and dried. The desired compound was obtained through decoloring by activated carbon and recrystallization with toluene.

Target compounds were prepared by the above mentioned process with various 4-chloro pyrimidine derivatives and various substituted phenols, parts of the results are as following:

Under the protection of N$_2$, 2-methylphenol (4.2 mmol) was added to 30 mL anhydrous DMF, and agitated to dissolve, then 2-(4-Cyanoanilino)-4-chloro benzo pyrimidine (3.5 mmol) was added and agitated to dissolve, after addition of anhydrous K$_2$CO$_3$ (0.021 mol), the temperature was controlled at 90~100° C. and the system was agitated to keep reaction for 8 h. When TLC shows that the reaction was complete, K$_2$CO$_3$ was filtered out, and the filtrate was poured into 300 mL cold water, solid was deposited; the solid was filtered out and dried. The desired compound was obtained through decoloring by activated carbon and recrystallization with toluene.

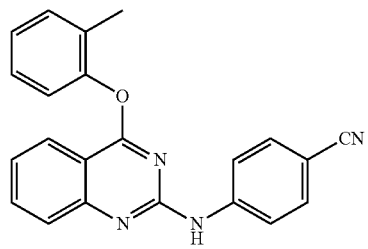

25

Brown powder, yield: 75% ; mp; 197.3-197.4° C.; $^1$HNMR (DMSO-d$_6$) δ (ppm) 2.16 (s, 3H, CH$_3$), 7.30-7.44 (m, 4H, Ar'H), 7.49 (td, 1H, J=7.6 Hz, J'=1.2 Hz, ArH$_7$), 7.56 (d, 2H, J=8.8 Hz, Ar"H$_{2,6}$), 7.72 (d, 1H, J=8.4 Hz, ArH$_6$), 7.86 (d, 2H, J=8.8 Hz, Ar"H$_{3,5}$), 7.90 (td, 1H, J=7.6 Hz, J'=1.2 Hz, ArH$_8$), 8.27 (dd, 1H, J=8.0 Hz, J'=0.8 Hz, ArH$_9$), 10.04 (s, 1H, NH). $^{13}$C NMR (DMSO-d$_6$) δ (ppm) 16.4 (CH$_3$), 102.8 (Ar"C$_4$), 112.2 (ArC$_5$), 118.9 (2C, Ar"C$_{2,6}$), 120.0 (CN), 122.9 (ArC$_6$), 124.2 (Ar'C$_6$), 124.8 (ArC$_7$), 125.9 (ArC$_9$), 126.7 (Ar'C$_4$), 128.0 (Ar'C$_5$), 130.7 (Ar'C$_3$), 131.9 (ArC$_8$), 133.1 (Ar'C$_2$), 135.4 (2C, Ar"C$_{3,5}$), 145.4 (Ar"C$_1$), 151.4 (Ar'C$_1$), 153.1 (ArC$_{10}$), 155.7 (ArC$_2$), 167.2 (ArC$_4$).

MS (ESI) m/z 353 (M$^+$+1).

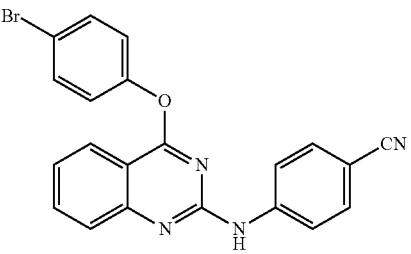

26

The operation was the same as above mentioned. Yellow acicular crystal, yield: 85%; mp: 267.3-267.6° C.; $^1$H NMR (DMSO-d$_6$) δ (ppm) 7.41 (d, 2H, J=6.8 Hz, Ar"H$_{2,6}$), 7.47 (t, 1H, J=7.2 Hz, ArH$_7$), 7.61 (d, 2H, J=8.8 Hz, Ar'H$_{2,6}$), 7.71-7.75 (m, 3H, ArH$_6$+Ar"H$_{3,5}$), 7.88 (td, 1H, J=8.4 Hz, J'=1.2 Hz, ArH$_8$), 7.94 (d, 2H, J=8.4 Hz, Ar'H$_{3,5}$), 8.21 (d, 1H, J=8.4 Hz, ArH$_9$), 10.02 (s, 1H, NH).

$^{13}$C NMR (DMSO-d$_6$) δ (ppm) 103.0 (Ar"C$_4$), 112.5 (ArC$_5$), 118.8 (2C, Ar"C$_{2,6}$), 119.0 (2C, Ar'C$_{2,6}$), 120.0 (CN), 124.2 (Ar'C$_4$), 124.8 (ArC$_6$), 125.2 (2C, Ar'C$_{3,5}$), 126.0 (ArC$_7$), 133.1 (ArC$_9$), 133.2 (2C, Ar"C$_{3,5}$), 135.5 (ArC$_8$), 145.3 (Ar"C$_1$), 152.2 (ArC$_{10}$), 153.1 (Ar'C$_1$), 155.4 (ArC$_2$), 167.4 (ArC$_4$).

MS (ESI) m/z 417 (M$^+$+1).

27

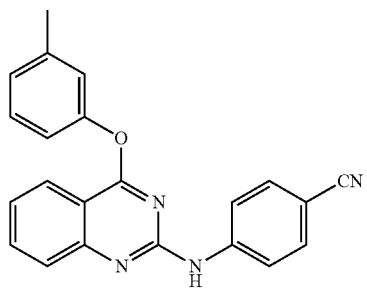

The operation was the same as above mentioned. White acicular crystal solid, yield: 98.3%; mp:219.7-220.3° C.; $^1$H NMR (DMSO-d$_6$) δ (ppm) 2.39 (s, 3H, CH$_3$), 7.18-7.22 (m, 3H, Ar'H), 7.43 (d, 1H, J=7.6 Hz, Ar'H), 7.48 (td, 1H, J=8.0 Hz, J'=1.2 Hz, ArH$_7$), 7.59 (d, 2H, J=8.4 Hz, Ar"H$_{2,6}$), 7.72 (d, 1H, J=8.4 Hz, ArH$_6$), 7.88 (td, 1H, J=7.2 Hz, J'=1.2 Hz, ArH$_8$), 7.93 (d, 2H, J=8.4 Hz, Ar"H$_{3,5}$), 8.22 (dd, 1H, J=8.4 Hz, J'=1.2 Hz, ArH$_9$), 10.03 (s, 1H, NH).

$^{13}$C NMR (DMSO-d$_6$) δ (ppm) 20.8 (CH$_3$), 102.3 (Ar"C$_4$), 112.0 (ArC$_5$), 118.4 (2C, Ar"C$_{2,6}$), 119.0 (CN), 119.4 (ArC$_6$), 122.4 (Ar'C$_6$), 123.6 (Ar'C$_2$), 124.1 (ArC$_7$), 125.3 (ArC$_9$), 126.5 (Ar'C$_4$), 129.5 (Ar'C$_5$), 132.6 (2C, Ar"C$_{3,5}$), 134.8 (ArC$_8$), 139.6 (Ar'C$_3$), 144.8 (Ar"C$_1$), 152.3 (ArC$_{10}$), 152.5 (Ar'C$_1$), 155.0 (ArC$_2$), 167.1 (ArC$_4$).

MS (ESI) m/z 353 (M$^+$+1).

28

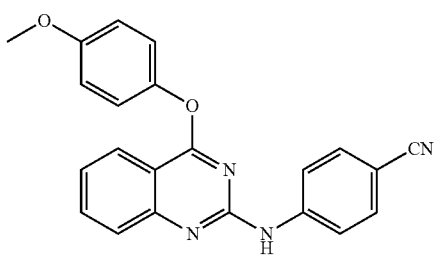

The operation was the same as above mentioned. White flocculus solid, yield:89.1%; mp: 218.2-218.4° C.; $^1$H NMR (DMSO-d$_6$) δ (ppm) 3.83 (s, 3H, CH$_3$O), 7.08 (d, 2H, J=6.8 Hz, Ar'H$_{3,5}$), 7.32 (d, 2H, J=6.8 Hz, Ar'H$_{2,6}$), 7.47 (td, 1H, J=8.0 Hz, J'=0.8 Hz, ArH$_7$), 7.59 (d, 2H, J=8.8 Hz, Ar"H$_{2,6}$), 7.71 (d, 1H, J=8.4 Hz, ArH$_6$), 7.87 (td, 1H, J=8.4 Hz, J'=1.2 Hz, ArH$_8$), 7.95 (d, 2H, J=8.4 Hz, Ar"H$_{3,5}$), 8.21 (dd, 1H, J=8.4 Hz, J'=1.2 Hz, ArH$_9$), 9.99 (s, 1H, NH).

$^{13}$C NMR (DMSO-d$_6$) δ (ppm) 56.0 (CH$_3$O), 102.9 (Ar"C$_4$), 112.6 (ArC$_5$), 115.3 (2C, Ar'C$_{3,5}$), 119.0 (2C, Ar"C$_{2,6}$), 120.1 (CN), 123.5 (2C, Ar'C$_{2,6}$), 124.2 (ArC$_6$), 124.7 (ArC$_7$), 125.9 (ArC$_9$), 133.2 (ArC$_8$), 135.3 (2C, Ar"C$_{3,5}$), 145.4 (Ar"C$_1$), 146.2 (Ar'C$_1$), 153.0 (ArC$_{10}$), 155.6 (Ar'C$_4$), 157.6 (ArC$_2$), 167.9 (ArC$_4$).

MS (ESI) m/z 369 (M$^+$+1).

Example 3-2

Synthesis of the Diaryl Benzo Pyrimidine Derivative (Method Two)

2-methoxyphenol and 2-chloro benzo pyrimidine derivative were mixed together, and heated to 150~210° C. until the reactants melt completely, and frit reaction lasts for 1 h. When the TLC demonstrates that the reaction was complete, the reaction mixture was dissolved into DMF, decolored with activated carbon and filtered, the filtration was poured into cold water; the deposited solid was filtered out and dried. The desired compound was obtained through recrystallization with toluene.

29

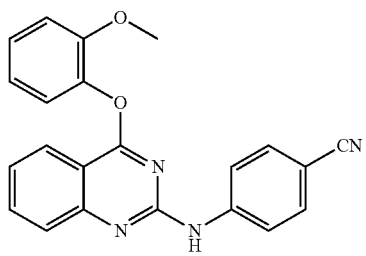

White flocculus solid, yield: 82.9%; mp: 220.0-220.5° C.; $^1$H NMR (DMSO-d$_6$) δ (ppm) 3.73 (s, 3H, CH$_3$O), 7.10 (td, 1H, J=7.6 Hz, J'=1.6 Hz, Ar'H$_6$), 7.30 (dd, 1H, J=8.4 Hz, J'=1.2 Hz, Ar'H$_3$), 7.35-7.41 (m, 2H, Ar'H$_{4,5}$), 7.47 (td, 1H, J=8.0 Hz, J'=0.8 Hz, ArH$_7$), 7.56 (d, 2H, J=8.8 Hz, Ar"H$_{2,6}$), 7.71 (d, 1H, J=8.4 Hz, ArH$_6$), 7.84 (d, 2H, J=8.8 Hz, Ar"H$_{3,5}$), 7.89 (td, 1H, J=8.4 Hz, J'=1.2 Hz, ArH$_8$), 8.22 (d, 1H, J=8.4 Hz, ArH$_9$), 10.06 (s, 1H, NH).

$^{13}$C NMR (DMSO-d$_6$) δ (ppm) 55.8 (CH$_3$O), 102.3 (Ar"C$_4$), 111.6 (ArC$_5$), 113.4 (Ar'C$_3$), 118.3 (2C, Ar"C$_{2,6}$), 119.5 (CN), 121.0 (ArC$_6$), 123.1 (Ar'C$_5$), 123.8 (ArC$_7$), 124.2 (Ar'C$_6$), 125.4 (ArC$_9$), 127.2 (Ar'C$_4$), 132.6 (2C, Ar"C$_{3,5}$), 134.9 (ArC$_8$), 140.9 (Ar"C$_1$), 144.9 (Ar'C$_1$), 151.1 (ArC$_{10}$), 152.6 (Ar'C$_2$), 155.2 (ArC$_2$), 166.8 (ArC$_4$).

MS (ESI) m/z 367 (M$^+$−1).

30

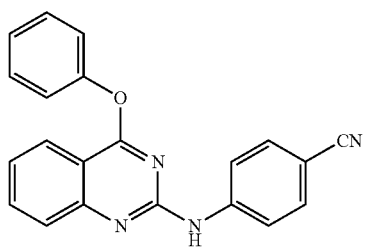

The operation was the same as above mentioned. White powder, yield: 89.6%; mp: 230.7-231.9° C.; $^1$H NMR (DMSO-d$_6$) δ (ppm) 7.38-7.43 (m, 3H, Ar"H$_{2,6}$+Ar'H$_4$), 7.48 (t, 1H, J=7.6 Hz, ArH$_7$), 7.55-7.59 (m, 4H, Ar'H$_{3,5}$+Ar'H$_{2,6}$), 7.72 (d, 1H, J=8.0 Hz, ArH$_6$), 7.87-7.91 (m, 3H, Ar"H$_{3,5}$+ArH$_8$), 8.23 (d, 1H, J=8.0 Hz, ArH$_9$), 10.04 (s, 1H, NH).

$^{13}$C NMR (DMSO-d$_6$) δ (ppm) 102.3 (Ar"C$_4$), 112.0 (ArC$_5$), 118.5 (2C, Ar"C$_{2,6}$), 119.5 (CN), 122.2 (2C, Ar'C$_{2,6}$), 123.7 (ArC$_6$), 124.2 (ArC$_7$), 125.4 (Ar'C$_4$), 126.0 (ArC$_9$), 129.9 (2C, Ar"C$_{3,5}$), 132.6 (2C, Ar"C$_{3,5}$), 134.9 (ArC$_8$), 144.8 (Ar"C$_1$), 152.4 (ArC$_{10}$), 152.6 (Ar'C$_1$), 155.1 (ArC$_2$), 167.2 (ArC$_4$).

MS (ESI) m/z 337 (M$^+$−1).

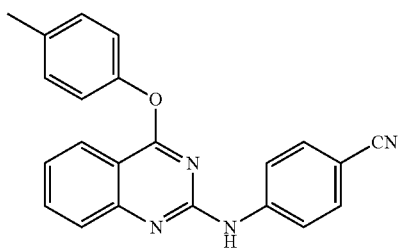

31

The operation was the same as above mentioned. White flocculus solid, yield: 86.6%; mp: 220.6-220.8° C.; $^1$H NMR (DMSO-d$_6$) δ (ppm) 2.39 (s, 3H, CH$_3$), 7.26 (d, 2H, J=8.8 Hz, Ar"H$_{2,6}$), 7.33 (d, 2H, J=8.4 Hz, Ar'H$_{3,5}$), 7.46 (t, 1H, J=8.0 Hz, ArH$_7$), 7.58 (d, 2H, J=8.4 Hz, Ar'H$_{2,6}$), 7.70 (d, 1H, J=8.4 Hz, ArH$_6$), 7.87 (td, 1H, J=8.0 Hz, J'=1.6 Hz, ArH$_8$), 7.94 (d, 2H, J=8.8 Hz, Ar"H$_{3,5}$), 8.20 (dd, 1H, J=8.4 Hz, J'=0.8 Hz, ArH$_9$), 9.98 (s, 1H, NH).

$^{13}$C NMR (DMSO-d$_6$) δ (ppm) 20.5 (CH$_3$), 102.4 (Ar"C$_4$), 112.1 (ArC$_5$), 118.5 (2C, Ar"C$_{2,6}$), 119.5 (CN), 121.8 (2C, Ar'C$_{2,6}$), 123.7 (ArC$_6$), 124.2 (ArC$_7$), 125.4 (ArC9), 130.2 (2C, Ar'C$_{3,5}$), 132.6 (2C, Ar"C$_{3,5}$), 134.8 (ArC$_8$), 135.1 (Ar'C$_4$), 144.9 (Ar"C$_1$), 150.1 (ArC$_{10}$), 152.5 (Ar'C$_1$), 155.1 (ArC$_2$), 167.2 (ArC$_4$).

MS (ESI) m/z 351 (M$^+$−1).

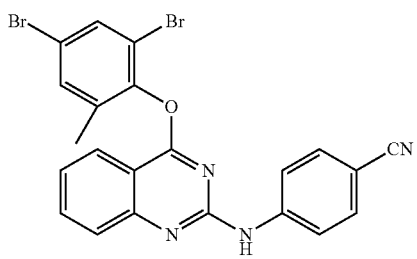

32

The operation was the same as above mentioned. Yellow acicular solid, yield: 79.4%; mp: 218.6-220.2° C.; $^1$HNMR (DMSO-d$_6$) δ (ppm) 2.20 (s, 3H, CH$_3$), 7.51 (t, 1H, J=7.6 Hz, ArH$_7$), 7.61 (d, 2H, J=8.8 Hz, Ar"H$_{2,6}$), 7.73-7.76 (m, 2H, Ar'H$_5$+ArH$_6$), 7.88-7.94 (m, 4H, ArH$_8$+Ar'H$_5$+Ar"H$_{3,5}$), 8.27 (d, 1H, J=8.0 Hz, ArH$_9$), 10.09 (s, 1H, NH).

$^{13}$C NMR (DMSO-d$_6$) δ (ppm) 16.3 (CH$_3$), 102.6 (Ar"C$_4$), 111.2 (ArC$_5$), 117.6 (Ar'C4), 118.5 (2C, Ar"C$_{2,6}$), 118.9 (CN), 119.5 (ArC$_6$), 123.6 (Ar'C$_2$), 124.5 (ArC$_7$), 125.6 (ArC$_9$), 132.7 (ArC$_8$), 132.8 (2C, Ar"C$_{3,5}$), 133.3 (Ar'C$_3$), 135.3 (Ar'C$_5$), 135.5 (Ar'C$_6$), 144.7 (Ar"C$_1$), 147.6 (ArC$_{10}$), 152.8 (Ar'C$_1$), 154.9 (ArC2), 165.2 (ArC$_4$).

MS (ESI) m/z 511 (M$^+$+1).

Effect Example 1

Anti HIV Biological Activity Test

NVP, DLV and EFV were used as control substances, the inhibitory activities of part of the target compounds are shown in Table 1.

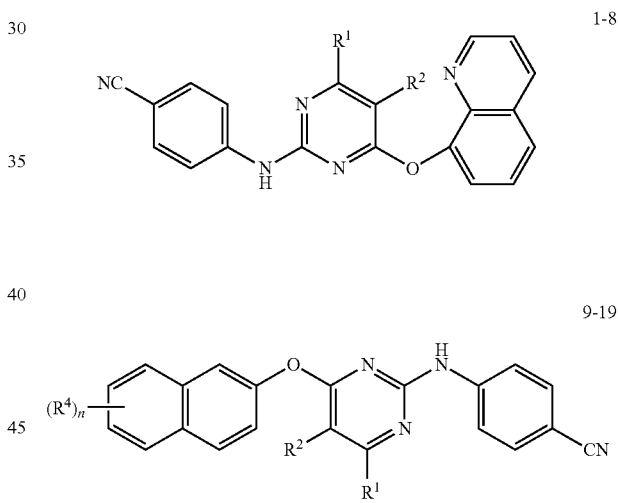

TABLE 1

Anti-HIV activities and cell toxicities of Compounds 1-32 on MT-4 cells

| | | | | EC50 | | | |
|---|---|---|---|---|---|---|---|
| Compounds | R1 | R2 | R4 | HIV-1(IIIB) (nM) | 103N + 181C (μM) | CC$_{50}$ (μM) | SI[b] |
| 1 | H | H | | 2.9 | 38.84 | 38.84 | 13393 |
| 2 | Cl | H | | 19.5 | 20.11 | 20.10 | 1031 |
| 3 | NHCH3 | H | | 8.9 | 54.20 | 54.19 | 6089 |
| 4 | OCH3 | H | | 12.8 | 42.23 | 42.23 | 3299 |
| 5 | H | Me | | 5.8 | 19.91 | 19.91 | 3432 |
| 6 | Cl | Me | | 25.7 | 44.72 | 44.72 | 1740 |
| 7 | NHCH3 | Me | | 15.8 | 36.53 | 36.53 | 2312 |
| 8 | OCH3 | Me | | 17.8 | 31.82 | 31.81 | 1787 |
| 9 | Cl | i-Pr | 6-CN | 50.0 | 3.36 | 435.55 | 8711 |
| 10 | H | H | 1-Me | 3.46 | 11.00 | 114.11 | 32981 |
| 11 | H | H | 3-Me | 2.3 | >70.94 | 71.16 | 30941 |

TABLE 1-continued

Anti-HIV activities and cell toxicities of Compounds 1-32 on MT-4 cells

| Compounds | R1 | R2 | R4 | EC50 HIV-1(IIIB) (nM) | EC50 103N + 181C (μM) | CC50 (μM) | SI[b] |
|---|---|---|---|---|---|---|---|
| 12 | H | H | 1,3-diMe | 4.1 | 1.17 | 313.39 | 76436 |
| 13 | H | H | 1,6-diBr | 4.6 | >50.39 | 51.06 | 11099 |
| 14 | H | H | 6-CN | 3.3 | 6.30 | 67.81 | 20548 |
| 15 | H | H | 1-Br-6-CN | 1.6 | 0.24 | 290.00 | 181247 |
| 16 | H | H | 3-Br-6-CN | 1.1 | >56.53 | 55.39 | 50357 |
| 17 | NHCH3 | Me | 1-Br | 15.4 | 6.15 | 177.01 | 11494 |
| 18 | NHCH3 | Et | 1-Br-6-CN | 6.2 | >59.52 | 303.92 | 49020 |
| 19 | NHCH3 | i-Pr | 6-CN | 7.6 | 4.58 | 265.00 | 34868 |
| NVP | | | | 75.1 | — | 5.41 | >72 |
| DLV | | | | 72 | — | 0.86 | 12 |
| EFV | | | | 3 | 560 | 4.30 | >1434 |

[a]IC$_{50}$: the concentration of an inhibitor that is required for 50% inhibition of HIV-1 RT;
[b]SI: Selectivity index, the ratio of CC$_{50}$/IC$_{50}$.

The results show that the compounds included by the general chemical formula possess strong anti HIV-1 virus activity, slight cell toxicity and high selectivity index; and a part of the compounds also exhibit certain anti HIV-2 action, this is different from the classical NNRTIs.

Effect Example 2

Anti HIV-1 Biological Activity Test

Screening for in vitro activity of anti HIV-1 reverse transcriptase (HIV-1 RT) (tested by The National Center for Drug Screening), the materials and methods were as following:
1. HIV-1 RT: Extracted in the lab and stored.
2. Sample treatment: sample was dissolved in DMSO to achieve suitable concentration before use, and 10-fold diluted with double distilled water, 8 dilution degrees per sample (sample was not dissolved completely in double distilled water).
3. Positive control medicine: nevirapine (NVP), Nanjing Zezhong Medical & Chemical Information Research Center.
4. Test method: after dilution, the sample was added to the reaction buffer containing Biotin-dUTP and genetically engineered target enzyme to incubate under optimal reaction conditions, avidin labeled horseradish peroxidase system was used as colour reagent, and the value of OD450 was determined.

The inhibitory activities of parts of target compounds are shown in Table 2.

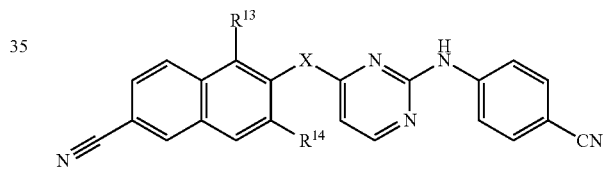

TABLE 2

Biological activities of the compounds to wild type, mutant type HIV-1 and HIV-1 RT

| Compounds | R13 | R14 | X | IC$_{50}$[a] (ug/ml) | EC50[b] WT(IIIB) (nM) | EC50[b] 103N + 181C (nM) | CC$_{50}$ (μM) | SI[d] |
|---|---|---|---|---|---|---|---|---|
| 20 | OMe | H | O | 0.9 | 1.2 | 380 | 160.84 | ≥134032 |
| 21 | H | OMe | O | 0.52 | 0.9 | 318070 | 142.41 | >158228 |
| 22 | OMe | OMe | O | 0.04 | 0.8 | 160 | 20.00 | ≥25000 |
| 23 | Cl | H | O | — | 1.8 | 700 | 86.34 | 47964 |
| 24 | Cl | OMe | O | — | 0.6 | 150 | 15.42 | ≥25701 |
| NVP | | | | 0.37 | 75.1 | — | 5.41 | >72 |
| DLV | | | | | 72 | — | 0.86 | 12 |
| EFV | | | | | 3 | 560 | 4.30 | >1434 |

[a]IC$_{50}$: the concentration of an inhibitor that is required for 50% inhibition of HIV-1 RT;
[b]EC$_{50}$: half effect concentration, drug concentration that is required for half of individuals to produce a specific effect;
[c]CC$_{50}$: drug concentration required to reduce cell viability by 50%, i.e. drug concentration that is required for 50% cell death;
[d]SI: Selectivity index, the ratio of CC$_{50}$/IC$_{50}$.

The results show that, the compounds included by the general chemical formula are non-nucleoside reverse transcriptase inhibitors, and possess strong anti-HIV-1 virus activity, and slight cell toxicity and high selectivity index; and most of the compounds showed good inhibition ability against drug-resistant viral strain of L103N+Y181C.

Effect Example 3

Anti-HIV Biological Activity Test

HEPT and DDI were used as control substances, the inhibitory activities of a part of the target compounds are shown in Table 3.

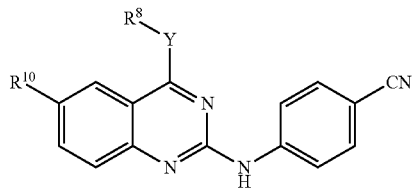

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. A compound or pharmaceutically acceptable salts thereof, wherein the compound has the structure shown as the formula I:

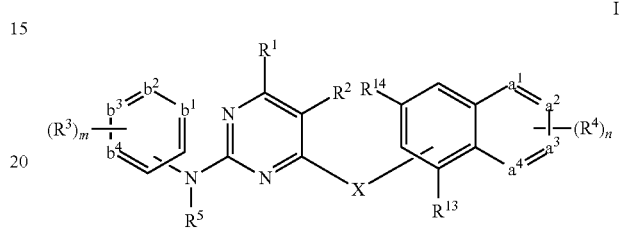

TABLE 3

Anti-HIV activities and cell toxicities of compounds 25-54 on MT-4 cells

| Compounds | $R^{10}$ | $R^8$ | Y | $EC_{50}$ (nM)[a] HIV-1(IIIB) | $CC_{50}$ (μM)[b] | SI[c] |
|---|---|---|---|---|---|---|
| 25 | H | 2-Me—Ph | O | 93.7 | 107.6 | 1148 |
| 26 | H | 4-Br—Ph | O | 263 | 235.1 | 894 |
| 27 | H | -3-Me—Ph | O | 625 | >351.9 | >563 |
| 28 | H | 4-MeO—Ph | O | 187 | >3397.4 | >1810 |
| 29 | H | 2-MeO—Ph | O | 30 | >185.6 | >6186 |
| 30 | H | Ph | O | 887 | >364.6 | >411 |
| 31 | H | 4-Me—Ph | O | 42 | 339.8 | 8091 |
| 32 | H | 2,4-diBr-6-Me—Ph | O | 17.6 | 156.9 | 8917 |
| 33 | H | -4-CN-2-Me—Ph | O | 28 | >333.0 | >11893 |
| 34 | H | 2,4,6-triBr—Ph | O | 23 | 71 | 3087 |
| 35 | H | 2,6-diBr-4-Me—Ph | O | 15 | 23.4 | 1563 |
| 36 | H | 2,4,6-triMe—Ph | O | 23 | >34.1 | >1484 |
| 37 | H | 2,4-diCl—Ph | O | 28 | 113.9 | 4068 |
| 38 | H | 4-F—Ph | O | 156 | 310.0 | 1987 |
| 39 | H | 2-Cl—Ph | O | 57 | 343 | 6018 |
| 40 | H | 4-Cl—Ph | O | 167 | >395.6 | >2369 |
| 41 | H | 4-CN-2,6-diMeO—Ph | O | 2.2 | >93.1 | >42311 |
| 42 | H | 2,4,6-triCl—Ph | O | 3.5 | 244.4 | 69833 |
| 43 | H | 2,6-diMe—Ph | O | 46 | >639.5 | >13902 |
| 44 | H | Ph | S | 752 | 494.1 | 657 |
| 45 | H | 4-CN-2,6-diMe—Ph | O | 3.6 | >172.2 | >47832 |
| 46 | H | 4-CN-2,6-diEtO—Ph | O | 2.9 | >99.3 | >34239 |
| 47 | H | 4-CN-2-EtO-6-$^n$PrO—Ph | O | 3.2 | >66.7 | >20842 |
| 48 | H | 2-Cl-4-CN-6-MeO—Ph | O | 5.6 | >173.0 | >30899 |
| 49 | H | 2-Cl-4-CN-6-EtO—Ph | O | 5.9 | >594.1 | >10692 |
| 50 | H | 4-CN-2-MeO-6-$^i$PrO—Ph | O | 6.7 | >65.8 | >9823 |
| 51 | H | Ph | $SO_2$ | 589 | >215.0 | >365 |
| 52 | H | 4-CN-2-EtO-6-MeO—Ph | O | 2.6 | >130.3 | >50129 |
| 53 | H | 4-CN-2-MeO-6- | O | 5.4 | >57.7 | >10691 |
| 54 | Cl | 2,4,6-Me—Ph | O | 1.8 | 147.0 | 81672 |
| | | BOE/BIRG587(nevirapine) | | 75.1 | >15.02 | >252 |
| | | DDN/AZT | | 5.17 | >93.548 | >18094 |
| | | DMP266(efavirenz) | | 3 | >6.336 | >2174 |

[a]$IC_{50}$: the concentration of an inhibitor that is required for 50% inhibition of HIV-1 RT;
[b]$CC_{50}$: drug concentration required to reduce cell viability by 50%, i.e. drug concentration that is required for 50% cell death;
[c]SI: Selectivity index, the ratio of $CC_{50}/IC_{50}$.

The results show that, the compounds included by the general chemical formula generally possess strong anti-HIV-1 virus activity, and slight cell toxicity and high selectivity index.

wherein -$a^1$=$a^2$-$a^3$=$a^4$- represents the structure of a divalent free radical and is selected from: —CH═CH—CH═CH—, —N═CH—CH═CH—, —CH═N—CH═CH—, —N═N—CH═CH—, —N═CH—N═CH—, —N═CH—CH═N—;

-b¹=b²-b³=b⁴- represents the structure of a divalent free radical and is selected from: —CH═CH—CH═CH—, —N═CH—CH═CH—, —N═N—CH═CH—, —N═CH—N═CH—, —N═CH—CH═N—;

R¹ and R² respectively are separately selected from hydrogen, hydroxyl, halogen, substituted $C_{1-4}$ alkyl, substituted $C_{2-6}$ alkenyl, substituted $C_{2-6}$ alkynyl, $C_{1-6}$ alkoxyl, cyano-group, nitryl, amino-group, —NH(OH)—, —N(R⁶)p—;

R¹³ and R¹⁴ respectively are separately selected from hydrogen, hydroxyl, halogen, substituted $C_{1-4}$ alkyl, substituted $C_{2-6}$ alkenyl, substituted $C_{2-6}$ alkynyl, $C_{1-6}$ alkoxyl, cyano-group, nitryl, amino-group, —NH(OH)—, —N(R⁶)p—;

R³ and R⁴ respectively are separately selected from hydrogen, hydroxyl, halogen, $C_{1-6}$ alkyl substituted by cyano-group or —C(═O)R⁶, $C_{3-7}$ cycloalkyl, $C_{2-6}$ alkenyl substituted by one or more halogen atoms or cyano-groups, $C_{2-6}$ alkynyl substituted by one or more halogen atoms or cyano-groups, $C_{1-6}$ alkoxycarbonyl, carboxyl, cyano-group, nitryl, amino-group, —NR⁵—, methyl polyhalide, methoxyl polyhalide, methylthio polyhalide, —S(═O)$_p$R⁷, —NH—S(═O)$_p$R⁷, —C(═O)R⁷, —NHC(═O)H, —C(═O)NHNH₂, —NHC(═O)R⁷, and —C(═NH)R⁷;

R⁵ represents hydrogen, $C_{1-6}$ alkycarbonyl, aryl, formoxyl, $C_{1-6}$ alkyl, $C_{1-6}$ alkoxycarbonyl;

X is selected from —NR⁶—, —NH—NH—, —N═N—, —O—, —C(═O)—, $C_{1-4}$ alkanediyl, —CHOH—, —S—, —S(═O)p—, -X₁-$C_{1-4}$ alkanediyl- or -$C_{1-4}$ alkanediyl-X₁-, and —CH(CN)—;

X₁ is selected from —NR⁶—, —NH—NH—, —N═N—, —O—, —C(═O)—, —CHOH—, and —S(═O)p—;

R⁶ is separately selected from hydrogen, aryl, formoxyl, $C_{1-6}$ alkycarbonyl, $C_{1-6}$ alkyl, $C_{1-6}$ alkoxycarbonyl, $C_{1-6}$ alkyl substituted by formoxyl, $C_{1-6}$ alkycarbonyl, $C_{1-6}$ alkoxycarbonyl or $C_{1-6}$ alkycarboxyl, $C_{1-6}$ alkoxyl and $C_{1-6}$ alkoxycarbonyl substituted by $C_{1-6}$ alkoxycarbonyl;

R⁷ is selected from amino-group-, —NH—NH—, mono- or di-($C_{1-4}$ alkyl) amino-group and $C_{1-4}$ alkyl polyhalide, wherein where R³ is —S(═O)$_p$R⁷, R⁷ is selected from —NH—NH— and $C_{1-4}$ alkyl polyhalide;

m is an integer from 0 to 5, n is an integer from 0 to 6; and

P is an integer of 1 or 2.

2. The compound or pharmaceutically acceptable salts thereof of claim 1, wherein the compound has the structure shown as the formula II:

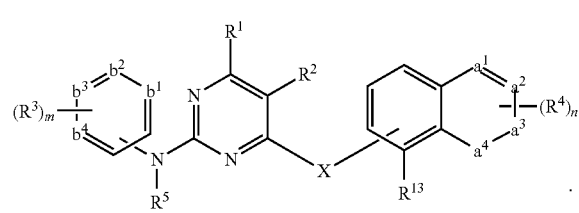

3. The compound or pharmaceutically acceptable salts thereof of claim 1, wherein the compound has the structure shown as the formula III:

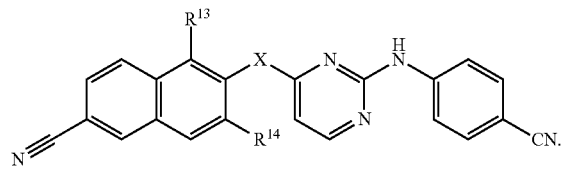

4. The compound or pharmaceutically acceptable salts thereof of claim 1, wherein the salts are selected from hydrochloride, sulfate, tartrate, citrate, fumarate, and malate.

5. A compound or pharmaceutically acceptable salts thereof, wherein the compound has the structure shown as the formula IV

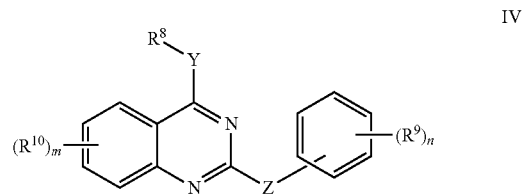

wherein R⁸ is separately selected from aryl, substituted aryl, naphthyl, substituted naphthyl, 5- or 6-membered aromatic heterocyclic, $C_{1-6}$ alkoxycarbonyl, aryloxycarbonyl, and substituted aryloxycarbonyl;

R⁹ and R¹⁰ respectively are separately selected from hydrogen, hydroxyl, halogen, $C_{1-6}$ alkoxyl, $C_{1-6}$ alkoxycarbonyl, carboxyl, cyano-group, nitryl, amino-group, —NR¹¹—, methyl polyhalide, methoxyl polyhalide, methylthio polyhalide, —S(═O)$_p$R¹², —NH—S(═O)$_p$R¹², —C(═O)R¹², —NHC(═O)H, —C(═O)NHNH₂, —NHC(═O)R¹², and —C(═NH)R¹²;

Z and Y respectively are separately selected from —NR¹¹—, —NH—, —NH—NH—, —N═N—, —O—, —C(═O)—, $C_{1-4}$ alkanediyl, —CH(OH)—, —S—, —S(═O)p—, -X₂-$C_{1-4}$ alkanediyl, -$C_{1-4}$ alkanediyl-X₂-, and —CH(CN)—;

X² is selected from —NR¹¹—, —NH—NH—, —N═N—, —O—, —C(═O)—, —CH(OH)—, and —S(═O)p—;

R¹¹ is separately selected from aryl, formoxyl, $C_{1-6}$ alkycarbonyl, $C_{1-6}$ alkyl, $C_{1-6}$ alkoxycarbonyl, $C_{1-6}$ alkyl substituted by formoxyl, $C_{1-6}$ alkycarbonyl, $C_{1-6}$ alkoxycarbonyl or $C_{1-6}$ alkycarboxyl, $C_{1-6}$ alkoxyl and $C_{1-6}$ alkoxycarboxyl substituted by $C_{1-6}$ alkoxycarbonyl;

R¹² is selected from $C_{1-4}$ alkyl, amino-group, mono- or di-($C_{1-4}$ alkyl) amino-group and $C_{1-4}$ alkyl polyhalide;

m is an integer from 0 to 5, n is an integer from 0 to 6; and

P is an integer of 1 or 2.

6. The compound of claim 5, wherein the pharmaceutically acceptable salts are selected from hydrochloride, sulfate, tartrate, citrate, fumarate, and malate.

7. The compound of claim 1, wherein X is —O—.

8. The compound of claim 5, wherein Z is —O—.

9. The compound of claim 1, wherein R3 is the cyano-group.

10. A pharmaceutical composition, wherein the pharmaceutical composition comprises an effective dosage of a compound or pharmaceutically acceptable salts thereof of claim 1, and pharmaceutically acceptable carriers.

11. A pharmaceutical composition, wherein the pharmaceutical composition comprises an effective dosage of a compound or pharmaceutically acceptable salts thereof of claim 5, and pharmaceutically acceptable carriers.

12. A method of manufacturing a medicament, comprising mixing a compound or pharmaceutically acceptable salts thereof in accordance with claim 1 with a pharmaceutically acceptable carrier.

13. A method of manufacturing a medicament, comprising mixing a compound or pharmaceutically acceptable salts thereof in accordance with claim 5 with a pharmaceutically acceptable carrier.

14. A method for preparing the compound in accordance with claim 5, comprising:
(a) mixing 4-chloro benzo pyrimidine, substituted phenol or aniline, and polar aprotic solvent to react according to the following general equation to obtain the compound in accordance with claim 5;

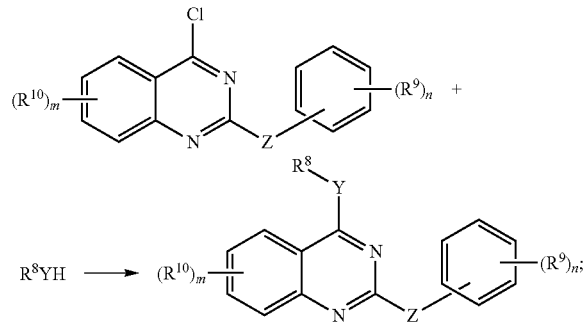

or, comprising:
(b) heating 2-chloro benzo pyrimidine and substituted phenol or aniline to 150° C.-210° C. to fuse to react according to the following general equation, to obtain the compound according to claim 5;

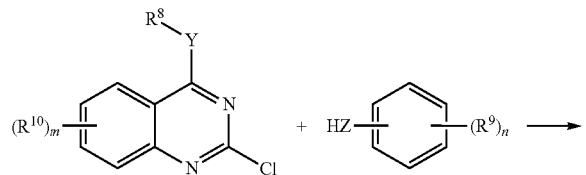

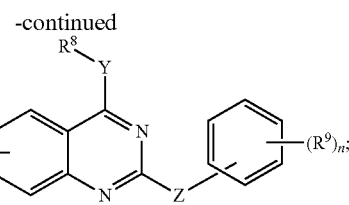

wherein, $R^8$ is separately selected from aryl, substituted aryl, naphthyl, substituted naphthyl, 5- or 6-membered aromatic heterocyclic, $C_{1-6}$ alkoxycarbonyl, aryloxycarbonyl, and substituted aryloxycarbonyl;

$R^9$ and $R^{10}$ respectively are separately selected from hydrogen, hydroxyl, halogen, $C_{1-6}$ alkoxyl, $C_{1-6}$ alkoxycarbonyl, carboxyl, cyano-group, nitryl, amino-group, —$NR^{11}$—, methyl polyhalide, methoxyl polyhalide, methylthio polyhalide, —$S(=O)_pR^{12}$, —NH—$S(=O)_pR^{12}$, —$C(=O)R^{12}$, —$NHC(=O)H$, —$C(=O)NHNH_2$, —$NHC(=O)R^{12}$, and —$C(=NH)R^{12}$;

Z and Y respectively are separately selected from —$NR^{11}$—, —NH—, —NH—NH—, —N=N—, —O—, —C(=O)—, $C_{1-4}$ alkanediyl, —CH(OH)—, —S—, —$S(=O)p$—, -$X_2$-$C_{1-4}$ alkanediyl, -$C_{1-4}$ alkanediyl-$X_2$-, and —CH(CN)—;

$X_2$ is selected from —$NR^{11}$—, —NH—NH—, —N=N—, —O—, —C(=O)—, —CH(OH)—, and —$S(=O)p$—;

$R^{11}$ is separately selected from aryl, formoxyl, $C_{1-6}$ alkycarbonyl, $C_{1-6}$ alkyl, $C_{1-6}$ alkoxycarbonyl, $C_{1-6}$ alkyl substituted by formoxyl, $C_{1-6}$ alkycarbonyl, $C_{1-6}$ alkoxycarbonyl or $C_{1-6}$ alkycarboxyl, $C_{1-6}$ alkoxyl and $C_{1-6}$ alkoxycarbonyl substituted by $C_{1-6}$ alkoxycarbonyl;

$R^{12}$ is selected from $C_{1-4}$ alkyl, amino-group, mono- or di-($C_{1-4}$ alkyl) amino-group and $C_{1-4}$ alkyl polyhalide.

m is an integer from 0 to 5, n is an integer from 0 to 6; and P is an integer of 1 or 2.

15. The method of claim 14, wherein the reaction of step (a) is under the protection of inert gas, wherein the inert gas is argon, nitrogen, helium, or combinations thereof.

16. The method of claim 14, wherein the aprotic solvent used in step (a) is acetonitrile, N,N-dimethylformamide, N,N-dimethylacetamide, tetrahydrofuran, or combinations thereof.

17. The method of claim 14, wherein bases used in step (a) are selected from potassium carbonate, sodium carbonate, cesium carbonate, sodium hydride, sodium hydroxide, and potassium hydroxide.

* * * * *